(12) United States Patent
Wakayama

(10) Patent No.: US 11,564,950 B2
(45) Date of Patent: Jan. 31, 2023

(54) COMPOSITION AND METHOD FOR PRODUCING THE SAME

(71) Applicant: LAIMU CORPORATION, Yokohama (JP)

(72) Inventor: Sachio Wakayama, Yokohama (JP)

(73) Assignee: LAIMU CORPORATION, Kanagawa (JP)

( * ) Notice: Subject to any disclaimer, the term of this patent is extended or adjusted under 35 U.S.C. 154(b) by 967 days.

(21) Appl. No.: 16/081,087

(22) PCT Filed: Jun. 15, 2018

(86) PCT No.: PCT/JP2018/022911
§ 371 (c)(1),
(2) Date: Aug. 30, 2018

(87) PCT Pub. No.: WO2019/058665
PCT Pub. Date: Mar. 28, 2019

(65) Prior Publication Data
US 2021/0177911 A1    Jun. 17, 2021

(30) Foreign Application Priority Data

Sep. 19, 2017   (JP) .............................. JP2017-178823

(51) Int. Cl.
| | | |
|---|---|---|
| *A61K 35/57* | (2015.01) | |
| *A23L 33/125* | (2016.01) | |
| *A23L 33/00* | (2016.01) | |
| *A61P 3/08* | (2006.01) | |
| *A61P 3/06* | (2006.01) | |
| *A61P 19/02* | (2006.01) | |
| *A61P 9/12* | (2006.01) | |
| *A61P 29/00* | (2006.01) | |
| *A61K 31/728* | (2006.01) | |

(52) U.S. Cl.
CPC ............ *A61K 35/57* (2013.01); *A23L 33/125* (2016.08); *A23L 33/40* (2016.08); *A61K 31/728* (2013.01); *A61P 3/06* (2018.01); *A61P 3/08* (2018.01); *A61P 9/12* (2018.01); *A61P 19/02* (2018.01); *A61P 29/00* (2018.01); *A23V 2002/00* (2013.01)

(58) Field of Classification Search
None
See application file for complete search history.

(56) References Cited

U.S. PATENT DOCUMENTS 4,328,803 A * 5/1982 Pape .................... A61F 9/00781
604/28
4,851,521 A * 7/1989 della Valle .......... C08B 37/0072
536/55.1

FOREIGN PATENT DOCUMENTS

| JP | 06-107556 A | 4/1994 |
|---|---|---|
| JP | 2002-145800 A | 5/2002 |
| JP | 2008-143856 A | 6/2008 |
| JP | 2009-102278 A | 5/2009 |
| JP | 2010-159216 A | 7/2010 |
| JP | 2017141392 A | 8/2017 |
| JP | 6303063 B1 | 3/2018 |
| JP | 6303064 B1 | 3/2018 |
| JP | 6303065 B1 | 3/2018 |
| JP | 6307201 B1 | 4/2018 |
| WO | 2009/113512 A1 | 9/2009 |

OTHER PUBLICATIONS

Srisantisaeng et al. (2013) J. Sci. Food Agric. 93: 3390-3394. (Year: 2013).*
Ariyoshi et al. (2005) JBC vol. 280, No. 19, 18967-18972. (Year: 2005).*
Maharja et al. (2011) PLoS One 6(10): 10 pages (Year: 2011).*
Ke et al. (2011) Food and Chemical Toxicology 49: 2670-2675. (Year: 2011).*
Da Rosa et al. (2012) Ciencia Rural. Santa Maria v. 42, n. 9: 1682-1687. (Year: 2012).*
Kalman et al. (2008) Nutrition Journal 7: 3 (9 pages). (Year: 2008).*
Kulkarni et al. (2018) J. Applied and Natural Science 10(1): 313-315. (Year: 2018).*
McArthur et al. (2012) Patient Preference and Adherence 6: 905-910. (Year: 2012).*
Nakano et al. (1991) Poultry Science 70: 2524-2528. (Year: 1991).*
Nakano et al. (1989) Poultry Science 68: 1303-1306. (Year: 1989).*
Borenstein (2004) Current Pain and Headache Reports, 8: 512-517. (Year: 2004).*
Gellhorn et al. (2013) Nat. Rev. Rheumatol. 9(4): 216-224. (Year: 2013).*
Goode et al. (2013) Curr. Rheumatol. Rep. 15: 301 (8 pages). (Year: 2013).*
Website document entitled: "When Back Pain is Caused by Spinal Arthritis" by Chris Iliades (Dec. 15, 2016). (available at everydayhealth.com/back-pain/arthritis-and-your-spine.aspx). (Year: 2016).*
International Search Report and Written Opinion of PCT/JP2018/022911 dated Sep. 4, 2018 with English Translation.
International Preliminary Report on Patentability of Chapter I, i.e., International Search Opinion of PCT/JP2018/022911 dated Apr. 2, 2020 with English Translation.
Supplemental European Search Report dated Jul. 26, 2021, from corresponding EP application No. EP 18 85 8549.
Hosokawa, et al., Effect of dietary hyaluronic acid (extra-cellular matrix: ECM-E) on analgesic activity and on the healing of experimental open wound in rat, Nihonyakugakukaiyoushishu, 2011, pp. 23-29, vol. 8.
Yamamoto, et al., Effect of dietary hyaluronic acid (extra-cellular matrix: ECM-E) on analgesic activity and on the healing of experimental open wound in rat, Nihonyakugakukaiyoushishu, 1998, p. 83, vol. 118th, No. 3.

(Continued)

*Primary Examiner* — Russell G Fiebig
(74) *Attorney, Agent, or Firm* — Browdy and Neimark, PLLC

(57) ABSTRACT

A degradation product produced by degrading a composition containing a hyaluronic acid and a protein with a protease has a pain relieving effect, a joint function ameliorating effect, a cholesterol-lowering effect, a hypoglycemic effect and a diastolic blood pressure-lowering effect.

6 Claims, 4 Drawing Sheets

(56) References Cited

OTHER PUBLICATIONS

Yamamoto, et al. Effect of dietary hyaluronic acid (extra-ecllular matrix: ECM-E) on analgesic activity and on the healing of experimental open wound in rat, Medicine and Biology, 1999, pp. 253-258, vol. 136(6).

* cited by examiner

EVALUATION OF KNEE JOINT PAIN RELIEVING EFFECT ACCORDING TO
THE JAPANESE VERSION OF KNEE OSTEOARTHRITIS PATIENT FUNCTION EVALUATION SCALE

EVALUATION OF KNEE JOINT PAIN RELIEVING EFFECT ACCORDING TO
THE WEST ONTARIO MCMASTER UNIVERSITY OSTEOARTHRITIS INDEX

EVALUATION OF PHYSICAL FUNCTION ACCORDING TO
THE WEST ONTARIO MCMASTER UNIVERSITY OSTEOARTHRITIS INDEX

EVALUATION OF LOW BACK PAIN RELIEVING EFFECT ACCORDING TO
LOW BACK PAIN PATIENT FUNCTION ASSESSMENT QUESTIONNAIRE

EVALUATION OF KNEE JOINT MOTION RANGE INCREASING EFFECT

VARIATION OF TOTAL CHOLESTEROL (T-cho)

COMPOSITION AND METHOD FOR PRODUCING THE SAME

TECHNICAL FIELD

The present invention relates to a composition and to a method for producing the composition.

BACKGROUND ART

Hyaluronic acid is known to have an action of enhancing a moisturizing effect and a water-retentive effect, and has heretofore been incorporated in various cosmetics and medicines. For example, hyaluronic acid is generally used by directly applying it to a dry skin or a rough skin so as to enhance the moisture-retaining property thereof for skin conditioning, or for preventing moisture from being lost from the skin surface in a dry season, hyaluronic acid is preventively applied to the skin surface. In addition, hyaluronic acid is expected to express a function derived from the moisturizing effect thereof or any other useful characteristics than the moisturizing effect, and some studies are known relating to new use thereof.

For example, PTL 1 proposes use of a degradation product produced by degrading a composition containing a hyaluronic acid and a protein with a protease, as a wound treatment agent. The wound treatment agent uses a hyaluronic acid and a protein that are biogenic substances, and a slow-reacting enzyme, and is therefore highly safe, and can quickly treat a wound, for example, through oral administration or direct administration to a region of wound.

CITATION LIST

Patent Literature

PTL 1: JP-2002-145800A

SUMMARY OF INVENTION

Technical Problem

As described above, a degradation product produced by degrading a composition containing a hyaluronic acid and a protein with a protease is highly useful as a wound treatment agent. However, the degradation product has been merely confirmed to have a wound treatment effect but any other effect thereof is almost unknown, and the application range of the product is limited.

On the other hand, recently, "antiaging" has come to attract great interest. "Antiaging" is to relieve a cause of age-related symptoms to thereby prevent or ameliorate a decline in physical function (aging). An age-related decline in physical function includes arthralgia at waist or knee, decrease in a range of joint motion, hypertension, and hypercholesterolemia or hyperglycemia caused by metabolic change, and aggravation of symptoms of such disorders may detract from the quality of life to pose various obstacle in a daily life. Consequently, various medicines, supplements and drinks have been developed and are taken routinely for the purpose of preventing and ameliorating such an age-related decline in physical function. However, such effects often vary between individuals, and already-existing products could not often provide a sufficient effect. In that situation, it is earnestly desired to develop a novel composition capable of ameliorating the above-mentioned, age-related decline in physical function.

Accordingly, for solving the problems in the existing technology, the present inventors have promoted investigations for the purpose of providing a novel composition capable of ameliorating arthralgia and weakening of joint function, physical change in metabolic function and hypertension. In addition, the inventors have further promoted investigations for providing a method for producing such a composition at low cost.

Solution to Problem

The present inventors have made assiduous studies for the purpose of solving the above-mentioned problems and, as a result, have found for the first time that a degradation product produced by degrading the above-mentioned composition known to have a wound healing effect, that is, the composition containing a hyaluronic acid and a protein, with a protease has a pain relieving effect, a joint function ameliorating effect, a cholesterol-lowering effect, a hypoglycemic effect and a diastolic blood pressure-lowering effect. With that, the present inventors have further found that, by utilizing these effects of the degradation product, a pain relief agent, a joint function improver, a cholesterol-lowering agent, a hypoglycemic agent and a diastolic blood pressure-lowering agent that are all highly safe can be provided at low cost. The present invention has been proposed based on these findings, and specifically has the following constitution.

[1] A composition containing a degradation product obtained by degrading a composition containing a hyaluronic acid and a protein with a protease, which is any of a pain relief agent, a joint function improver, a cholesterol-lowering agent, a hypoglycemic agent or a diastolic blood pressure-lowering agent.

[2] The composition according to [1], which is a pain relief agent.

[3] The composition according to [2], which is a knee joint pain relief agent.

[4] The composition according to [2], which is a low back pain relief agent.

[5] The composition according to [1], which is a joint function improver.

[6] The composition according to [5], which is an agent for increasing the range of knee joint motion.

[7] The composition according to [1], which is a cholesterol-lowering agent.

[8] The composition according to [1], which is a hypoglycemic agent.

[9] The composition according to [1], which is a diastolic blood pressure-lowering agent.

[10] The composition according to any one of [1] to [9], wherein the composition containing a hyaluronic acid and a protein is a comb.

[11] The composition according to any one of [1] to [10], wherein the degradation product contains a low-molecular hyaluronic acid having a molecular weight of 380 to 5000.

[12] The composition according to [11], wherein the content of the low-molecular hyaluronic acid having a molecular weight of 380 to 5000 is 10% by mass or more relative to the total amount of the composition.

[13] The composition according to [11] or [12], wherein the proportion of a low-molecular hyaluronic acid having a molecular weight of 1520 to 5000 is 60% by mass or more of the total amount of the low-molecular hyaluronic acid having a molecular weight of 380 to 5000.

[14] The composition according to any one of [1] to [13], wherein the content of N-acetylglucosamine is 0.01% by mass or less relative to the total amount of the composition.
[15] The composition according to any one of [1] to [14], wherein a total free amino acid amount is 2% by mass or more as a ratio by mass to the total amount of the composition, and a total protein amount is 2% by mass or more as a ratio by mass to the total amount of the composition.
[16] The composition according to [15], wherein the free amino acid contains at least one selected from isoleucine, P-aminoisobutyric acid, alanine, phenylalanine, aspartic acid, cystine and tyrosine.
[17] The composition according to any one of [1] to [16], containing a ground product obtained by grinding a freeze-dried product of the degradation product.
[18] The composition according to any one of [1] to [17], which is a medicinal composition.
[19] The composition according to any one of [1] to [17], which is a food.
[20] The composition according to any one of [1] to [17], which is a drink.
[21] The composition according to any one of [1] to [17], which is a cosmetic product.
[22] A method for producing a pain relief agent, a joint function improver, a cholesterol-lowering agent, a hypoglycemic agent or a diastolic blood pressure-lowering agent, including an enzyme treatment step of degrading a composition containing a hyaluronic acid and a protein with a protease.
[23] The production method according to [22], in which the composition containing a hyaluronic acid and a protein is a comb and which includes, prior to the enzyme treatment step, a step of chipping the comb into pieces of 0.5 cm square or more.
[24] The production method according to [22] or [23], which includes, after the enzyme treatment step, a step of freeze-drying the degradation product obtained in the enzyme treatment step, and then grinding it into a ground product.
[25] The production method according to any one of [22] to [24], which includes, after the enzyme treatment step, a purification step of purifying the degradation product obtained in the enzyme treatment step.

Advantageous Effects of Invention

The composition of the present invention has a pain relieving effect, a joint function ameliorating effect, a cholesterol-lowering effect, a hypoglycemic effect and a diastolic blood pressure-lowering effect, and can be effectively used in medications having these medicinal effects. According to the production method for the composition of the present invention, the composition having the above-mentioned useful effects can be produced at low cost.

DESCRIPTION OF EMBODIMENTS

Figure 1:
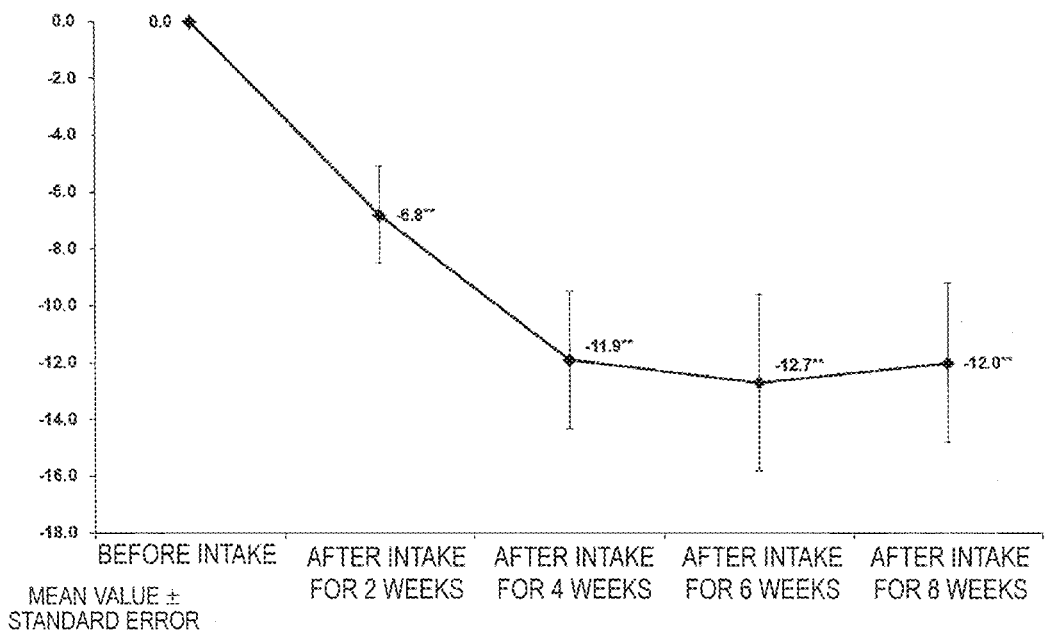
FIG. 1 This is a graph showing evaluation results of a knee joint pain relieving effect according to the Japanese version of a knee osteoarthritis patient function evaluation scale, after intake of protease-degraded product-containing capsules for a predetermined period of time.

The present invention is described in detail hereinunder. The description of the constitutive elements of the invention given hereinunder is for some typical embodiments or examples of the invention, to which, however, the invention should not be limited. In this description, the numerical range expressed by the wording "a number to another number" means the range that falls between the former number indicating the lower limit of the range and the latter number indicating the upper limit thereof.

[Composition]

The composition of the present invention is characterized by containing a degradation product obtained by degrading a composition containing a hyaluronic acid and a protein with a protease.

With no specific limitation, the hyaluronic acid contained in the composition may be any hyaluronic acid that is generally used as a component for cosmetics and medicines. Originally, a hyaluronic acid is isolated from a bovine vitreous body, but not limited thereto, any one isolated from an animal joint fluid or a cock's comb is usable here. Not one isolated from the natural field but any other obtained by synthesis or according to microbial fermentation may also be usable.

Hyaluronic acid is a complicated polysaccharide of amino acids and uronic acids, and the details of the structure are not specifically limited. For example, there can be mentioned a polysaccharide having a recurring unit of dioses of D-glucuronic acid and N-acetyl-D-glucosamine. The molecular weight of the hyaluronic acid contained in the composition is not specifically limited, and for example, the hyaluronic acid extracted from a cock's comb has a molecular weight of 6,000,000 to 10,000,000, but the hyaluronic acid extracted from a cock's comb has a mean molecular weight of hundreds of thousands to millions as it is degraded in the extraction process. The hyaluronic acid for use in the present invention may be an induced one or a thermally-denatured one so far as it does not too excessively lose at least one effect of a pain relieving effect, a joint function ameliorating effect, a cholesterol-lowering effect, a hypoglycemic effect and a diastolic blood pressure-lowering effect. Compounds known as so-called hyaluronic acid derivatives can be effectively used in the present invention.

The protein contained in the composition may be any one irrespective of the kind thereof, but is extremely preferably a protein contained in a comb. The kind of the comb is not specifically limited, but using a cock's comb is preferred. A cock's comb contains a hyaluronic acid and is therefore advantageous in that any additional hyaluronic acid does not need to be separately added thereto in providing the composition (composition containing a hyaluronic acid and a protein) for use for producing the composition of the present invention. Consequently, when a cock's comb is used, the production process for the composition of the present invention can be simplified and the production cost can be thereby reduced.

The composition for use in the present invention may contain only a protein and a hyaluronic acid, but may contain any other component, solvent or dispersion medium. The solvent and the dispersion medium may be any one capable of dissolving a protein and a hyaluronic acid, and water and an aqueous buffer are favorably used. The composition may be a natural substance itself containing a protein and a hyaluronic acid. The natural substance to be the composition includes an animal joint fluid and a comb, and a cock's comb is especially preferred as rich in a hyaluronic acid.

The degradation product for use in the present invention is one obtained by degrading the above-mentioned composition with a protease. The kind of the protease is not specifically limited. Any protease usable for ordinary proteolysis is usable here. Specifically, an endopeptidase or an exopeptidase is usable, and the active site may be any of serine, cystine, metal, aspartic acid, etc. Plural proteases may be mixed and used here. As a preferred protease, for example, a pronase may be used.

The degradation product for use in the present invention is one obtained by degrading the above-mentioned composition with a protease, and therefore contains at least a protein-degraded product that has been degraded with a protease, and a hyaluronic acid, and may contain an undegraded protein (a protein naturally contained in the composition before protease addition thereto) and any other component derived from the composition.

The protein-degraded product contained in the degradation product includes a protein, a peptide and a free amino acid having a lower molecular weight than that of the undegraded protein, and these may exist in the degradation product as mixed therein.

Preferably, the degradation product contains a free amino acid. The free amino acid that the degradation product contains may be a free amino acid as a protein-degraded product, or a free amino acid naturally contained in the composition before protease addition thereto. The kind of the free amino acid varies depending on the components of the composition. For example, in the degradation product from a composition of a comb, amino acids such as isoleucine, p-aminoisobutyric acid, alanine, phenylalanine, aspartic acid, cystine and tyrosine are contained in a relatively high content, and in addition to these, other various kinds of amino acids are contained therein.

The total protein amount in the composition of the present invention is preferably 0.5 to 10% by mass as a ratio by mass to the total amount of the composition, more preferably 1 to 7% by mass, even more preferably 2 to 5% by mass. The total free amino acid amount in the composition of the present invention is preferably 0.5 to 12% by mass as a ratio by mass to the total amount of the composition, more preferably 1 to 8% by mass, even more preferably 2 to 6% by mass. When the total protein amount and the free amino acid amount in the composition of the present invention each fall within the above-mentioned range, the composition is considered to effectively act so as to noticeably exhibit a pain relieving effect, a joint function ameliorating effect, a cholesterol-lowering effect, a hypoglycemic effect and a diastolic blood pressure-lowering effect.

In this description, the "total protein amount" means a total protein content determined according to a Lowry method; and the "total free amino acid amount" is a total amount of free amino acids determined according to a ninhydrin method.

The hyaluronic acid contained in the degradation product may be the hyaluronic acid that has been naturally contained in the composition before protease addition and has remained therein as such (hereinafter referred to as "undegraded hyaluronic acid"), or a degradation product of a hyaluronic acid (hereinafter referred to as "low-molecular hyaluronic acid"), or a mixture of the undegraded hyaluronic acid and the low-molecular hyaluronic acid, and preferably, the degradation product contains a low-molecular hyaluronic acid. A low-molecular hyaluronic acid can readily penetrate into the depth of a living organism and can effectively act on a living organism. The low-molecular hyaluronic acid that the degradation product contains may be a low-molecular hyaluronic acid obtained by hydrolyzing the hyaluronic acid in the composition, or a low-molecular hyaluronic acid prepared by hydrolyzing a hyaluronic acid in a system different from the composition and adding obtained low-molecular hyaluronic acid to the degradation product. Preferably, a low-molecular hyaluronic acid obtained by hydrolyzing the hyaluronic acid in the composition is contained in the degradation product. For producing a low-molecular hyaluronic acid in the composition, a substance capable of hydrolyzing a hyaluronic acid, such as hydrochloric acid or hyaluronidase may be added to the composition in which the hyaluronic acid is to be hydrolyzed. In the case where the composition is a natural substance, a low-molecular hyaluronic acid may be produced through autolysis with a substance originally contained in the natural substance. However, from the viewpoint of effectively realizing the action of a hyaluronic acid on a living organism, preferably, the hyaluronic acid maintains the structural unit thereof, that is, the hyaluronic acid is not degraded to glucuronic acid and N-acetyl glucosamine. Specifically, the N-acetylglucosamine content in the composition of the present invention is preferably 0.01% by mass or less relative to the total amount of the composition, and is most preferably 0% by mass.

In this description, the "N-acetylglucosamine amount" is an N-acetylglucosamine content determined according to a Morgan-Elson method.

The molecular weight of the low-molecular hyaluronic acid that the degradation product contains is preferably 380 to 5000. The molecular weight of 380 to 5000 corresponds to about 1 to 14 recurring units of hyaluronic acid. The content of the low-molecular hyaluronic acid having a molecular weight of 380 to 5000 in the composition of the present invention is preferably 5% by mass or more relative to the total amount of the composition, more preferably 7% by mass or more, even more preferably 10% by mass or more. Preferably, the main component of the low-molecular hyaluronic acid is a low-molecular hyaluronic acid having a molecular weight of 1520 to 5000, more preferably the proportion of a low-molecular hyaluronic acid having a molecular weight of 1520 to 5000 is 60% by mass or more of the total 5 amount of the low-molecular hyaluronic acid having a molecular weight of 380 to 5000, even more preferably 70% by mass or more, and further more preferably 75% by mass or more. With that, it is considered that the composition of the present invention can effectively act to noticeably exhibit a pain relieving effect, a joint function ameliorating effect, a cholesterol-lowering effect, a hypoglycemic effect and a diastolic blood pressure-lowering effect.

The molecular weight and the mass ratio of the low-molecular hyaluronic acid can be determined through analysis of high-performance liquid chromatography using polyethylene glycol as a molecular weight marker.

The properties of the degradation product vary depending on the components and the composition ratio of the composition and the kind of the protease to be used. In general, the degradation product is liquid, precisely viscous liquid. The degradation product may be used as the composition of the present invention directly as it is, but may be suitably purified and combined with any other component to be the composition of the present invention. By purifying the degradation product, a composition having a higher pain relieving effect, a higher joint function ameliorating effect, a higher cholesterol-lowering effect, a higher hypoglycemic effect and a higher diastolic blood pressure-lowering effect can be provided. A liquid composition can be used as an external preparation for external application or ocular instillation, or as an internal preparation of a type of drink. In the case where a degradation product is dried by freeze drying or the like and then ground, a powdery composition can be provided. The powdery composition can be used as an internal preparation directly as it is, or after mixed with any other component, or may be processed into tablets or capsules, or a desired solvent or dispersion medium may be added thereto to form a liquid, and the resultant liquid may be used as an external preparation for external application or ocular instillation, or as an internal preparation of a type of drink.

As in the above, the composition of the present invention may be provided in any form capable of exhibiting a pain relieving effect, a joint function ameliorating effect, a cholesterol-lowering effect, a hypoglycemic effect and a diastolic blood pressure-lowering effect. For example, the composition may be provided as medicines stated clearly to have these pharmaceutical potencies, quasi-drugs, functional foods (including supplementary foods, health foods, candies, chewing gums), functional drinks (including jelly drinks, solid-containing liquid drinks), functional cosmetics, and supplements, and these embodiments in use are interpreted to be included in the scope of the "composition" of the present invention.

The composition of the present invention may contain any other various components than the above-mentioned degradation product. For example, in the case where a vehicle is added to the composition, the blend ratio of the degradation product and the vehicle may be controlled to thereby control the component amount such as the total protein amount, the total free amino acid amount and the low-molecular hyaluronic acid amount. An embodiment of the composition that is easy to store is a mixture powder produced by diluting a ground powder of a freeze-dried degradation product with a vehicle. The vehicle is not specifically limited, but is preferably dextrin. The dilution ratio with the vehicle is preferably 2 to 10 times as a ratio by mass, more preferably 2 to 7 times, even more preferably 3 to 5 times.

The composition of the present invention has a pain relieving effect, a joint function ameliorating effect, a cholesterol-lowering effect, a hypoglycemic effect and a diastolic blood pressure-lowering effect. Accordingly, in the case where the composition of the present invention is taken orally and where the components thereof are absorbed by the intestinal tract, the composition improves the joint function and effectively prevents the pain of the joint. In addition, owing to the pain relieving effect, the sympathetic nerve can be prevented from being excited and the diastolic blood pressure can be effectively lowered to an appropriate level. Further, the component of the composition of the present invention can beneficially act on a lipid metabolic pathway and a sugar metabolic pathway to lower the cholesterol value and the blood sugar count to an appropriate level. Accordingly, an age-related decline in physical function can be effectively relieved. Here, the composition of the present invention is highly safe as using a hyaluronic acid and a protein that are biogenic substances and an enzyme that reacts mildly, and therefore has an advantage in that the composition can be used as an internal preparation to be taken orally with ease.

The amount of the composition of the present invention to be used varies depending on the targeted failure and is, for example, the following dose is preferred. For example, in the case where the composition of the present invention is orally administered as an internal preparation, the dose thereof is preferably 80 to 2000 mg/adult standard body weight/day, and multiple dosage of two or three times a day is suitable. The dose of the protease-degraded product is preferably 1 to 1500 mg/adult standard body weight/day.

[Method for Producing Composition]

Next, a method for producing the composition of the present invention is described.

A method for producing the composition of the present invention is characterized by including an enzyme treatment step of degrading a composition containing a hyaluronic acid and a protein with a protease.

The production method for the composition of the present invention may have, further if desired, any other step. For example, in the case where the composition is a comb, the production method may have a chipping step of chipping a comb, prior to the enzyme treatment step. In addition, the production method may have, after the enzyme treatment step, a filtration step of filtrating the degradation product, a powdering step of drying and grinding the filtrated degradation product, and a purification step of purifying the filtered degradation product. In the following, the production method for the composition of the present invention is described in detail.

First, a composition containing a hyaluronic acid and a protein is prepared. In the case where a cock's comb is used as the composition, any one is usable irrespective of age and sex. Preferably, however, a cock's comb is processed for protease degradation shortly after its collection. In the case where a cock's comb is processed for protease degradation long after its collection, preferably, it is once freeze-dried and then thawed before use.

In protease degradation of a comb, preferably, the comb is processed in a chipping step of chipping it, and then the resultant comb pieces are brought into contact with a protease-containing solution. The comb is preferably chipped into pieces of 0.5 cm square or more, more preferably 0.7 cm square or more, even more preferably 0.9 cm square or more. If too much chipped or minced, water may excessively flow out of the resultant pieces, unfavorably.

Next, the composition is processed in an enzyme treatment step of degrading it with a protease. Regarding the protease for use in the production method of the present invention, the description of protease in the column of [Composition] given hereinabove may be referred to.

Enzyme treatment varies depending on the kind of the composition and the protease. For example, in the case where the composition is a solid or a powder of a comb or the like, preferably, a solution such as an aqueous solution where a protease has been dissolved therein (enzyme solution) is added thereto and the left as such for a predetermined period of time. Here, the pH of the enzyme solution is preferably 5.0 to 10.0, the treatment temperature is preferably 40 to 60° C., and the treatment time is preferably 0.5 to 3.0 hours. Also preferably, the enzyme treatment is carried out while the composition to which the enzyme solution has been added is shaken.

From the degradation product obtained in the manner as above, a solid fraction of comb and others may be removed through filtration or the like, and the resultant liquid may be used as a liquid degradation product. If desired, the product may be further processed in a powdering step of drying it by freeze-drying or the like followed by further grinding it to give a powdery degradation product for use herein. The degradation product may be used as the composition of the present invention directly as it is, or may be used as the composition of the present invention after optionally purified or combined with any other component such as a vehicle.

The composition of the present invention may be produced according to such an extremely simple process. Therefore, using the production method for the composition of the present invention, a high-useful composition can be provided at low cost.

In addition, by purifying the filtered degradation product or the powdery degradation product, a composition having a higher pain relieving effect, a higher joint function ameliorating effect, a higher cholesterol-lowering effect, a higher hypoglycemic effect and a higher diastolic blood pressure-lowering effect can be provided. For the purification method for the degradation product, an ordinary purification method of liquid-liquid separation, column chromatography or the like may be employed.

[Use of Composition]

As described above, the composition of the present invention has a pain relieving effect, a joint function ameliorating effect, a cholesterol-lowering effect, a hypoglycemic effect and a diastolic blood pressure-lowering effect. Consequently, the composition of the present invention can be administered to animals including human beings and can be effectively used as a pain relief agent for relieving pain, a joint function improver for improving join function, a cholesterol-lowering agent for lowering a blood cholesterol level, a hypoglycemic agent for lowering a blood sugar level or a diastolic blood pressure-lowering agent for lowering a diastolic blood pressure. In particular, in addition, as a pain relief agent, the composition is favorably used as a knee joint pain relief agent or a low back pain relief agent; and as a joint function improver, the composition is favorably used as a knee joint motion range increasing agent for increasing the range of knee joint motion. In addition, the composition may be used as a medicine having both the two effects as combined. The composition as an internal preparation may optionally contain any other various components than the above-mentioned degradation product and vehicle. For example, vitamins, vegetable powders, minerals, yeast extracts, colorants and tackifiers may be optionally added thereto. The kind of these components is not specifically limited, and the content thereof may be appropriately controlled within a range capable of sufficiently exhibiting the intended function.

Examples

The present invention is described more specifically with reference to Examples given below. The materials, the ratio thereof and the operations in the following Examples may be appropriately varied not overstepping the scope and the spirit of the present invention. Accordingly, the range of the present invention should not be interpreted limitatively by the specific examples shown below.

Component analysis of the compositions produced in this Example was carried out according to the following methods.

(1) Measurement of Water Content

One g of the composition was heated and dried at 105° C. for 3 hours, and the constant weight thereof was measured with a precision balance to quantify the water content thereof.

(2) Total Nitrogen Determination

The total nitrogen was quantitatively determined according to a semimicro-Kjeldahl method based on an AOAC method.

(3) Free Amino Acid Determination and Amino Acid Composition Analysis

The total free amino acid amount was quantified according to a ninhydrin method. For quantification, a calibration curve of leucine as a standard amino acid was formed and used. The composition of the free amino acid was analyzed using an amino acid automatic analyzer (manufactured by Hitachi Limited, L-8500 Model) equipped with a column for bioanalysis. In the analysis, 50 mg of the composition was dissolved in distilled water, dried into solid under reduced pressure using a rotary evaporator (60° C.), then eluted with 5 mL of 0.02 N hydrochloric acid, and filtered through filter paper and then through a germ-free filter, and 50 μL of the resultant filtrate was used as an analysis sample.

(4) Protein Determination

The total protein amount was determined according to a Lawry method. A bovine serum albumin was used for forming a standard calibration curve.

(5) N-acetyl-D-glucosamine Determination

The N-acetyl-D-glucosamine content was determined according to a Morgan-Elson method.

(6) Glucosaminoglycan Determination

The sample was analyzed through colorimetry according to a 2-nitrophenylhydrazine coupling method. For standard calibration curve formation, comb-derived sodium hyaluronate (manufactured by Wako Pure Chemical Corporation, HARC) and *Streptococcus zooepidemicus*-derived sodium hyaluronate (manufactured by Wako Pure Chemical Corporation, HASZ) were used.

(7) Measurement of Molecular Weight of Low-Molecular Hyaluronic Acid

The molecular weight of hyaluronic acid was estimated through high-performance liquid chromatography (by Shimadzu Corporation) equipped with a differential refractometer (manufactured by Shimadzu Corporation, RID-10A Model). Columns of TSKgel G-2, 500PW$_{XL}$ (7.8 mm ID×30 cm) were used, and water was used as a mobile phase at a flow rate of 1 ml/min for analysis. As a molecular weight marker, four types of polyethylene glycol having a molecular weight of 400, 1000, 2000 or 6000 (manufactured by Aldrich Corp.) were used. The constituent weight ratio of each low-molecular hyaluronic acid was analyzed through high-performance liquid chromatography using samples of the pharmaceutical composition or dextrin alone, in which the peak area of dextrin was detracted from the peak area of the composition to determine the constituent weight ratio.

Production Example

One kg of freshly collected cock's combs were cut into small pieces of about 1 cm square, and thermally sterilized by steaming at 100° C. Food-derived enzymes mainly containing a protease were added to the small pieces and reacted at 45° C. for 1.5 hours, and then stirred and homogenized. Subsequently, rough solid fragments were removed by filtration to give a liquid degradation product (hereinafter referred to as "protease degradation product"). The protease degradation product had a pH of 6.5, a Brix value of 6.20 and a solid concentration of 5.91% by weight. The protease degradation product was freeze-dried and ground to be a freeze-dried powder of protease degradation product (composition 1). Dextrin in an amount of 3 equivalent times (as a ratio by mass) was added to the freeze-dried powder of protease degradation product to give a dextrin-added freeze-dried powder (composition 1').

[Component Analysis of Composition]

The produced composition 1' was analyzed for the constituent components thereof according to the above-mentioned method. The content of general components analyzed is shown in Table 1, the composition of free amino acids is shown in Table 2, and the analysis results of molecular weight of low-molecular hyaluronic acids are shown in Table 3. In Tables 1 to 3, "%" is "% by mass".

TABLE 1

General Components

|  | % |
|---|---|
| Water | 2.2-2.6 |
| Nitrogen | 3.84 |
| Total Protein | 3.04 |
| Free Amino Acid | 4.08 |
| N-acetylglucosamine | 0 |
| Dextrin (for food additive) | 75.0 |

TABLE 2

Free Amino Acid Composition

| Amino Acid | Content % | Amino Acid | Content % |
|---|---|---|---|
| ρ-serine | 1.71 | Cystine* | 2.78 |
| Taurine | 3.30 | Leucine* | 2.26 |
| Aspartic Acid* | 2.94 | Isoleucine* | 6.27 |
| Threonine* | 1.30 | Tyrosine* | 2.65 |
| Serine* | 2.20 | Phenylalanine* | 3.30 |
| Glutamic Acid* | 2.18 | β-aminoisobutyric Acid | 5.45 |
| Glutamine | 0.48 | Ornithine | 1.05 |
| Sarcosine | 1.81 | Lysine* | 1.17 |
| Glycine* | 2.26 | 1-Methylhystidine | 0.78 |
| Alanine* | 3.52 | Anserine | 1.92 |
| Citrulline | 0.92 | Arginine* | 1.93 |
| α-Aminobutyric Acid | 2.18 | Identified Total Amino Acids | 57.36 |
| Cystine* | 1.03 | Unknown Amino Acids | 42.64 |
| Methionine* | 1.97 | | |

*Protein composition amino acid

TABLE 3

Estimated Molecular Weight, Constituent Unit Number and Constituent Weight Ratio of Low-Molecular HA

| Peak No. | 1 | 2 | 3 | 4 | 5 |
|---|---|---|---|---|---|
| Estimated Molecular Weight | 5,000 | 1,520 | 1,140 | 760 | 380 |
| Constituent Unit Number | 13-14 | 4 | 3 | 2 | 1 |
| Constituent Weight Ratio (%) | 33 | 47 | 10 | 6 | 4 |

As shown in Table 2, among the free amino acids contained in the composition 1', the content of isoleucine and p-aminoisobutyric acid was high, and then, alanine, phenylalanine, aspartic acid, cystine and tyrosine were contained much.

As shown in Table 3, the composition 1' contained five types of low-molecular hyaluronic acids each having an estimated molecular weight of 5000, 1520, 1140, 760 and 380. When the molecular weight of one recurring unit of hyaluronic acid is about 400, the recurring unit number of each low-molecular hyaluronic acid is 13 to 14, 4, 3, 2 and 1 in that order from the largest molecular weight, and the mass ratio was 33%, 47%, 10%, 6% and 4%. Accordingly, it is known that the main components of the low-molecular hyaluronic acids are two components of a 4-molecular component having a molecular weight of about 1520, and a 13 to 14-molecular component having a molecular weight of about 5000. The content of the low-molecular hyaluronic acids having a molecular weight of 380 to 5000 in the composition 1' was 13.4% by mass relative to the total amount of the composition 1'.

[Preparation of Composition-Containing Capsule Formulation]

A dextrin-added freeze-dried powder (composition 1') prepared by adding dextrin to a freeze-dried, protease-degraded product powder in an amount of 3 times by equivalent (ratio by mass) was encapsulated in gelatin capsules to prepare a capsule formulation (hereinafter referred to as "protease-degraded product-containing capsules"). At this time, the amount of the freeze-dried, protease-degraded product powder that the capsules contained was 150 mg/capsule.

[Evaluation of Effects of Composition]

As test subjects, 12 healthy male and female adults (6 men, 6 women) suffering from knee or low back pain in their daily lives tried the freeze-dried powder of a protease-decomposed product produced in Production Example for evaluating the effect the powder. The age range of the subjects was 55 or more and less than 77. Specifically, before intake, each subject was requested to respond to a predetermined questionnaire or to undergo a predetermined examination, and after that, they took 4 protease-decomposed product-containing capsules twice a day along with water or lukewarm water, and after intake for 2 weeks, 4 weeks, 6 weeks or 8 weeks, they responded to a predetermined questionnaire or underwent a predetermined examination. Here, the dose of the capsule formulation corresponds to 600 mg once×two times=1200 mg as one-day intake amount of the freeze-dried, protease-decomposed product powder.

For statistical analysis, a statistical analysis system (SAS 9.4 produced by SAS Corporation, or SPSS Statistics 19 produced by IBM Corporation) was used, and the evaluation results before the start of intake and the evaluation results after the lapse of each test period were, as corresponding data, analyzed according to a t-test. The score obtained in the questionnaire survey was referred to as a non-parametric one, and for comparison in each group, a Wilcoxon's signed rank sum test was carried out. Here, a significant level is 5% on both sides, and the score falling within a range of 5% or more and less than 10% was judged to be marginally significant. In FIGS. 1 to 8 mentioned below, "*" indicates $p<0.05$, "**" indicates $p<0.01$, and "+" indicates $p<0.1$. The data may be expressed as a mean value±standard error.

(Evaluation of Knee Joint Pain Relieving Effect)

(1) Evaluation by Japanese Version of Knee Osteoarthritis Patient Function Evaluation Scale (JKOM)

Based on the Japanese version of a knee osteoarthritis patient function evaluation scale, the test subjects responded to a questionnaire relating to the degree of knee pain according to a VAS (visual analogue scale) method, before the start of intake of the protease-decomposed product-containing capsules and in 2 weeks, 4 weeks, 6 weeks and 8 weeks after the start of intake thereof, and to a questionnaire relating to their knee pain or rigidity, their condition in daily lives, their normal activities and health condition. With that, the total of the scores of the questionnaire results after the lapse of each intake period and the total of the scores of the questionnaire results before the start of intake were compared according to a Wilcoxon's signed rank sum test. The variations of the total of the scores after the lapse of each intake period, as based on the scores before the start of intake, are shown in FIG. 1.

Regarding the evaluation of pain degree according to a VAS method, one end of the straight line having a length of 100 mm was set as "no pain" and the other end thereof was as "severest pain ever experienced". With that, each test subject marked the degree of pain that he/she himself/herself felt on the straight line, and starting from the point with "no pain", the length marked by the test subject was measured. Regarding the score data of the questionnaire results, the lightest choice is "0", the severest choice is "4", and "1", "2" or "3" is given to the intermediate choice depending on the degree of severity of the symptom.

The total of the scores of the questionnaire results was 27.8±3.8 before intake, 21.0±2.9 after intake for 2 weeks, 15.9±3.0 after intake for 4 weeks, 15.2±2.9 after intake for 6 weeks, and 15.8±3.1 after intake for 8 weeks. As shown in FIG. 1, the variations based on the data before intake were −6.8±1.7 after intake for 2 weeks, −11.9±2.4 after intake for 4 weeks, −12.7±3.1 after intake for 6 weeks, and −12.0±2.8 after intake for 8 weeks. In time-dependent comparison, a significant decrease was recognized after intake for 2 weeks, after intake for 4 weeks, after intake for 6 weeks and after intake for 8 weeks, as compared with the data before intake.

(2) Evaluation by West Ontario McMaster University Osteoarthritis Index (Quasi-WOMAC Survey Slip)

Figure 2:
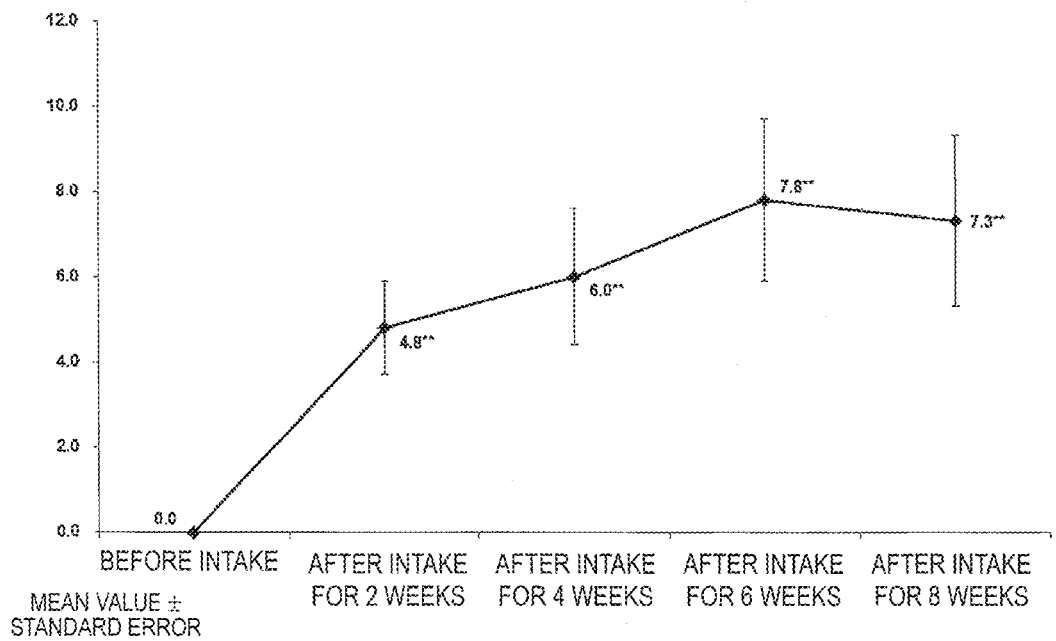
FIG. 2 This is a graph showing evaluation results of a knee joint pain relieving effect according to the West Ontario McMaster University osteoarthritis index, after intake of protease-degraded product-containing capsules for a predetermined period of time.

Based on the West Ontario McMaster University osteoarthritis index, the test subjects responded to a questionnaire regarding "right and left knees pain in the past 2 weeks" using the following reference indices, before the start of intake of the proteas-decomposed product-containing capsules, and in 2 weeks. 4 weeks, 6 weeks and 8 weeks after the start of intake. With that, the total of the scores of the questionnaire results after the lapse of each intake period and the total of the scores of the questionnaire results before the start of intake were compared according to a Wilcoxon's signed rank sum test. The variations of the total of the scores after the lapse of each intake period, as based on the scores before the start of intake, are shown in FIG. 2.

(Indices and Scores)
No pain at all: 5
Light pain: 4
Medium pain: 3
Strong pain: 2
Extremely severe pain: 1

The total of the scores of the questionnaire results was 37.3±1.9 before intake, 42.1±1.8 after intake for 2 weeks, 43.3±1.6 after intake for 4 weeks, 45.1±1.5 after intake for 6 weeks, and 44.6±1.5 after intake for 8 weeks. As shown in FIG. 2, the variations based on the data before intake were 4.8±1.1 after intake for 2 weeks, 6.0±1.6 after intake for 4 weeks, 7.8±1.9 after intake for 6 weeks, and 7.3±2.0 after intake for 8 weeks. In time-dependent comparison, a significant increase was recognized after intake for 2 weeks, 4 weeks, 6 weeks and 8 weeks, as compared with the data before intake.

Figure 3:
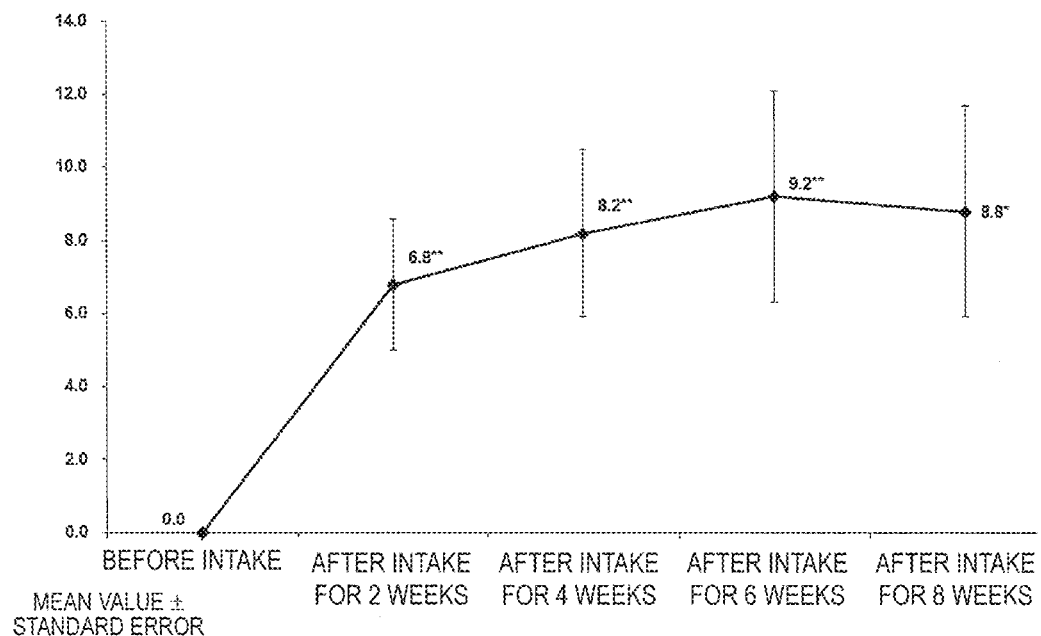
FIG. 3 This is a graph showing evaluation results of a physical function according to the West Ontario McMaster University osteoarthritis index, after intake of protease-degraded product-containing capsules for a predetermined period of time.

In addition, based on the West Ontario McMaster University osteoarthritis index, the test subjects responded to a questionnaire regarding "influence of the knee symptom on daily activities in the past 2 weeks" using the following reference indices, before the start of intake of the protease-decomposed product-containing capsules, and in 2 weeks, 4 weeks, 6 weeks and 8 weeks after the start of intake. With that, the total of the scores of the questionnaire results after the lapse of each intake period and the total of the scores of the questionnaire results before the start of intake were compared according to a Wilcoxon's signed rank sum test. The variations of the total of the scores after the lapse of each intake period, as based on the scores before the start of intake, are shown in FIG. 3.

(Indices and Scores)
No influence at all on daily activities: 5
Daily activities were a little difficult: 4
Daily activities were difficult in some degree: 3
Daily activities were difficult: 2
Daily activities were considerably difficult: 1

The total of the scores of the questionnaire results was 66.2±3.6 before intake, 73.0±2.5 after intake for 2 weeks, 74.3±2.7 after intake for 4 weeks, 75.3±2.5 after intake for 6 weeks, and 74.9±2.3 after intake for 8 weeks. As shown in FIG. 3, the variations based on the data before intake were 6.8±1.8 after intake for 2 weeks, 8.2±2.3 after intake for 4 weeks, 9.2±2.9 after intake for 6 weeks, and 8.8±2.9 after intake for 8 weeks. In time-dependent comparison, a significant increase was recognized after intake for 2 weeks, 4 weeks, 6 weeks and 8 weeks, as compared with the data before intake.

(Evaluation of Low Back Pain Relieving Effect)

Figure 4:
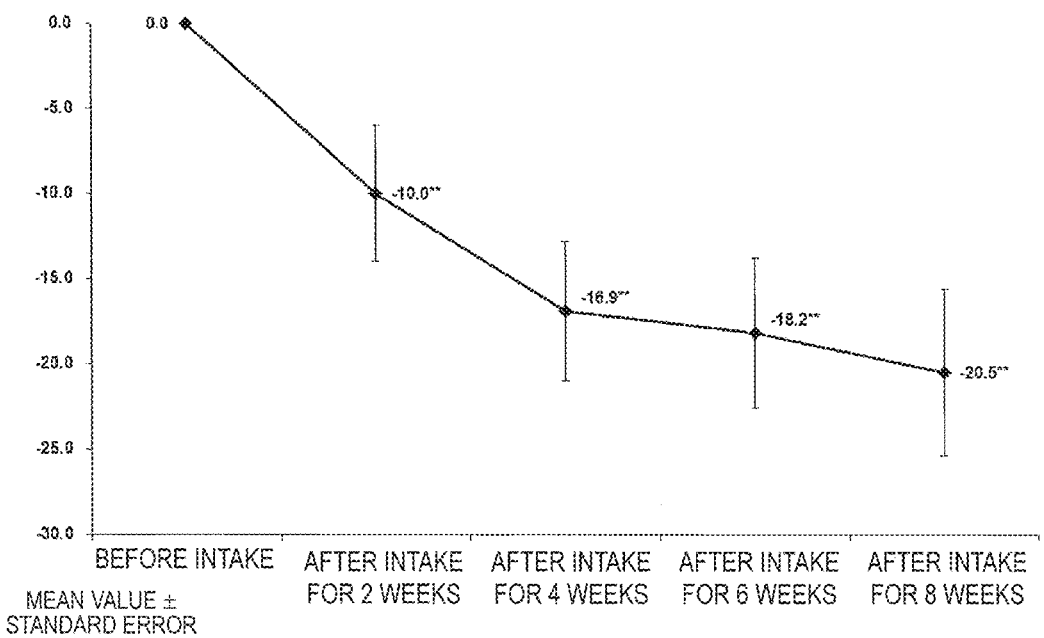
FIG. 4 This is a graph showing evaluation results of a low back pain relieving effect according to a low back pain patient function assessment questionnaire, after intake of protease-degraded product-containing capsules for a predetermined period of time.

Based on the Japan low back pain evaluation questionnaire (JLEQ), the test subjects responded to a questionnaire relating to the degree of knee pain according to a VAS method, before the start of intake of the protease-decomposed product-containing capsules and in 2 weeks, 4 weeks, 6 weeks and 8 weeks after the start of intake thereof, and to a questionnaire relating to their low back pain for a few days, and to their condition in daily lives owing to the low back pain for a few days. With that, the total of the scores of the questionnaire results after the lapse of each intake period and the total of the scores of the questionnaire results before the start of intake were compared according to a Wilcoxon's signed rank sum test. The variations of the total of the scores after the lapse of each intake period, as based on the scores before the start of intake, are shown in FIG. 4.

Regarding the evaluation of pain degree according to a VAS method, one end of the straight line having a length of 100 mm was set as "no pain" and the other end thereof was as "severest pain ever experienced". With that, each test subject marked the degree of pain that he/she himself/herself felt on the straight line, and starting from the point with "no pain", the length marked by the test subject was measured.

Regarding the score data of the questionnaire results, the lightest choice is "0", the severest choice is "4", and "1", "2" or "3" is given to the intermediate choice depending on the degree of severity of the symptom.

The total of the scores of the questionnaire results was 38.3±7.3 before intake, 28.3±6.5 after intake for 2 weeks, 21.3±5.5 after intake for 4 weeks, 20.1±4.3 after intake for 6 weeks, and 17.8±4.1 after intake for 8 weeks. As shown in FIG. 4, the variations based on the data before intake were −10.0±4.0 after intake for 2 weeks, −16.9±4.1 after intake for 4 weeks, −18.2±4.4 after intake for 6 weeks, and −20.5±4.9 after intake for 8 weeks. In time-dependent comparison, a significant decrease was recognized after intake for 2 weeks, 4 weeks, 6 weeks and 8 weeks, as compared with the data before intake.

[Evaluation of Knee Joint Motion Range Increasing Effect]

Figure 5:
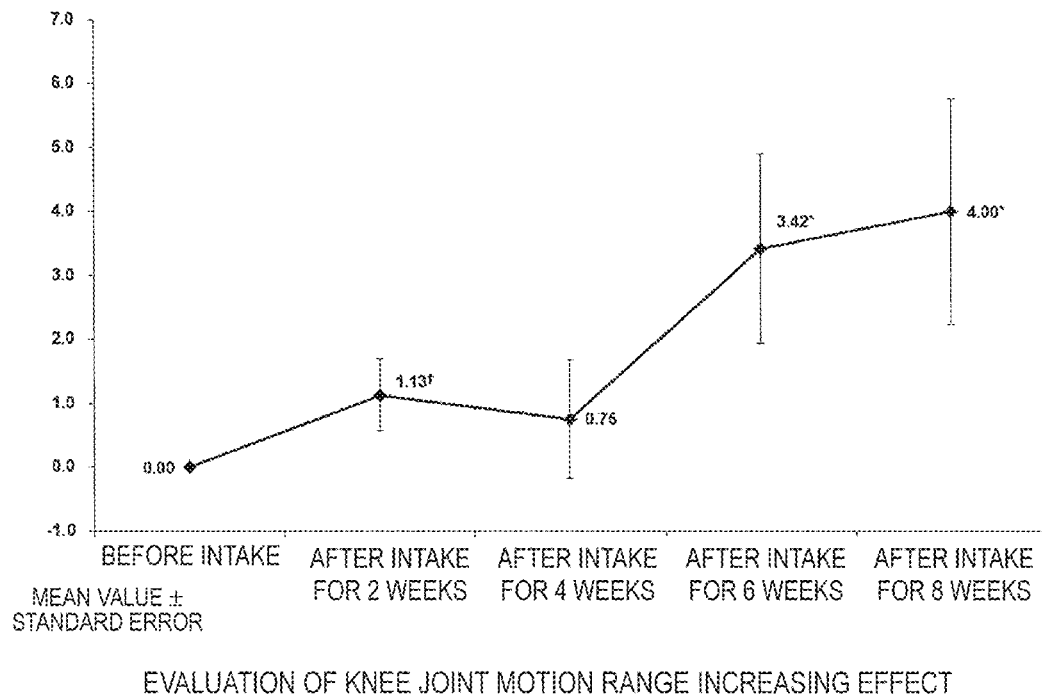
FIG. 5 This is a graph showing variations of a range of knee joint motion, after intake of protease-degraded product-containing capsules for a predetermined period of time.

Before the start of intake of the protease-degraded product-containing capsules and in 2 weeks, 4 weeks, 6 weeks and 8 weeks after the start of intake thereof, the range of knee joint motion was measured by orthopedic surgical specialists using a Tokyo University angle meter 30 cm (Z813-153A). The average value of the right and left knee joint motion ranges after the lapse of each intake time, and the average value of the right and left knee joint motion ranges before the start of intake were compared according to a t-test. The variations of the right and left knee joint motion ranges after the lapse of each intake period, as based on the data before the start of intake, are shown in FIG. 5.

The knee joint motion range was 137.38±1.81 degrees before intake, 138.50±1.71 degrees after intake for 2 weeks, 138.13±2.42 degrees after intake for 4 weeks, 140.79±1.62 degrees after intake for 6 weeks, and 141.38±1.77 degrees after intake for 8 weeks. As shown in FIG. 5, the variations based on the data before intake were 1.13±0.56 degrees after intake for 2 weeks, 0.75±0.93 degrees after intake for 4 weeks, 3.42±1.48 degrees after intake for 6 weeks, and 4.00±1.76 degrees after intake for 8 weeks. In time-dependent comparison, a significant increase was recognized after intake for 2 weeks, 4 weeks, 6 weeks and 8 weeks, as compared with the data before intake.

[Evaluation of Cholesterol-Lowering Effect and Hypoglycemic Effect]

Before the start of intake of the protease-degraded product-containing capsules and in 8 weeks after the start of intake thereof, a sample of each test subject was taken and analyzed for the total cholesterol level in blood (T-cho) and the glycohemoglobin level in blood (HbA1c). The measured data were compared before the start of intake and in 8 weeks after the start of intake according to a t-test. Here, glycohemoglobin (HbA1c) is one formed of blood glucose bonding to hemoglobin, and a higher blood glucose level expresses a higher glycohemoglobin level in blood (HbA1c).

Figure 6:
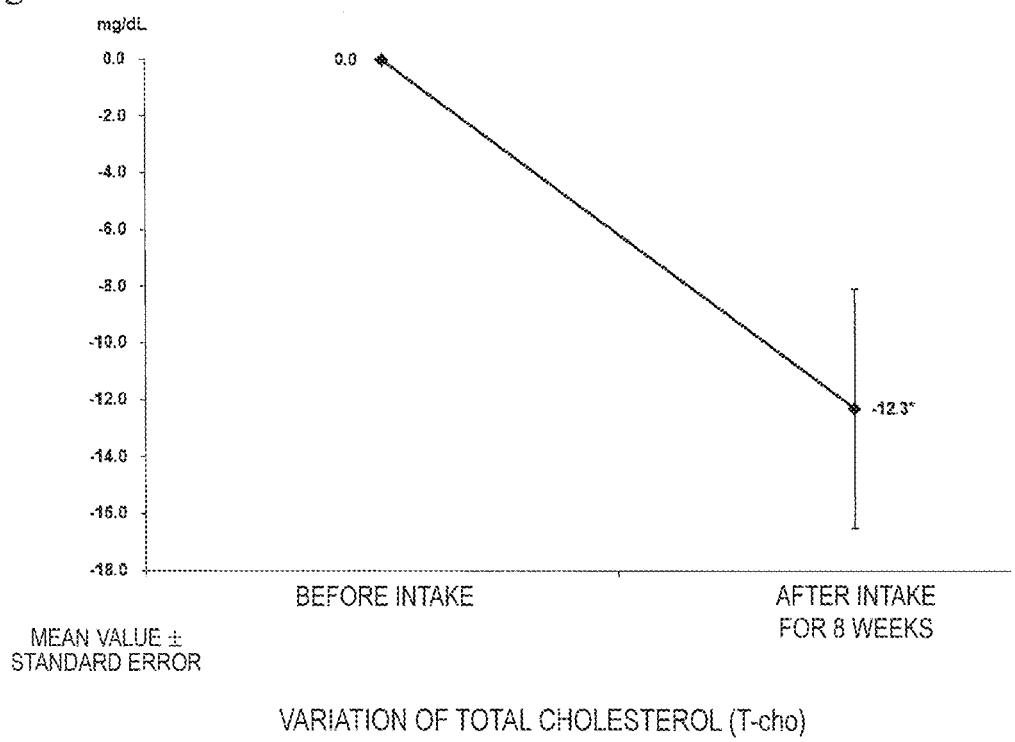
FIG. 6 This is a graph showing variations of a total cholesterol level in blood, after intake of protease-degraded product-containing capsules for 8 weeks.

The variations of the total cholesterol level in blood in 8 weeks after the start of intake, based on the data before the start of intake, are shown in FIG. 6.

The total cholesterol level in blood was 226.6±9.8 mg/dL before intake, and 214.3±7.9 mg/dL after intake for 8 weeks. As shown in FIG. 6, the variation based on the data before intake was −12.3±4.2 mg/dL after intake for 8 weeks. In time-dependent comparison, a significant decrease was recognized after intake for 8 weeks, as compared with the data before intake.

Figure 7:
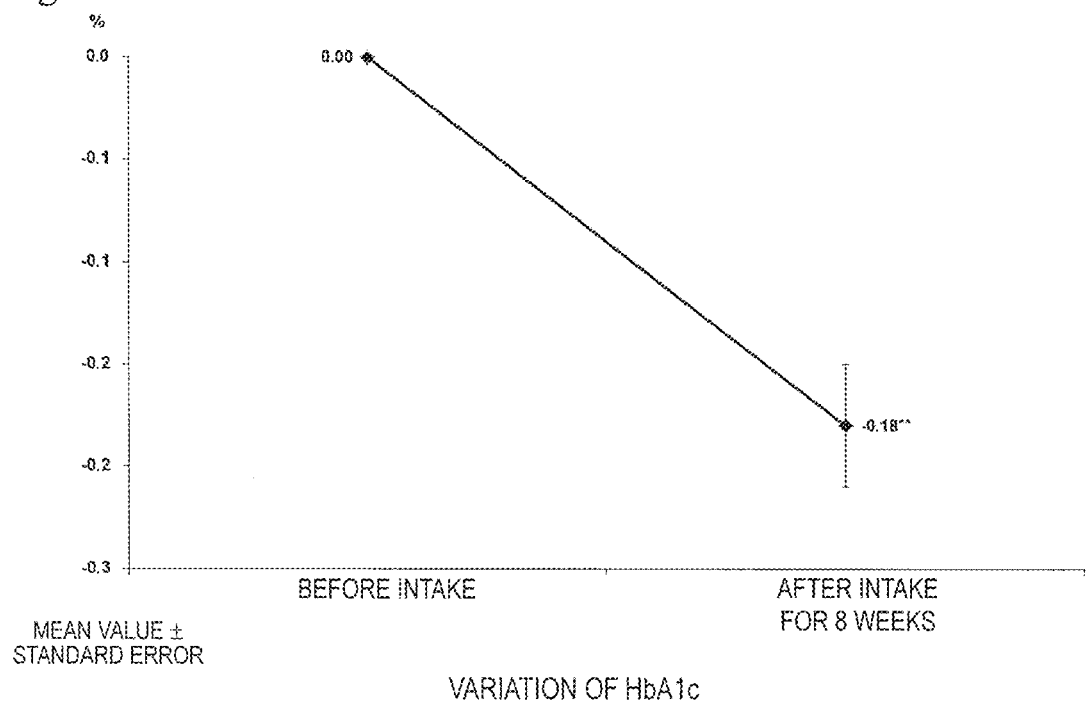
FIG. 7 This is a graph showing variations of a glycohemoglobin level in blood (HbA1c), after intake of protease-degraded product-containing capsules for 8 weeks.

The variations of the glycohemoglobin level in blood in 8 weeks after the start of intake, based on the data before the start of intake, are shown in FIG. 7.

The glycohemoglobin level in blood was 5.47±0.08% before intake, and 5.29±0.07% after intake for 8 weeks. As shown in FIG. 7, the variation based on the data before intake was −0.18±0.03% after intake for 8 weeks. In time-dependent comparison, a significant decrease was recognized after intake for 8 weeks, as compared with the data before intake.

[Evaluation of Diastolic Blood Pressure-Lowering Effect]

Figure 8:
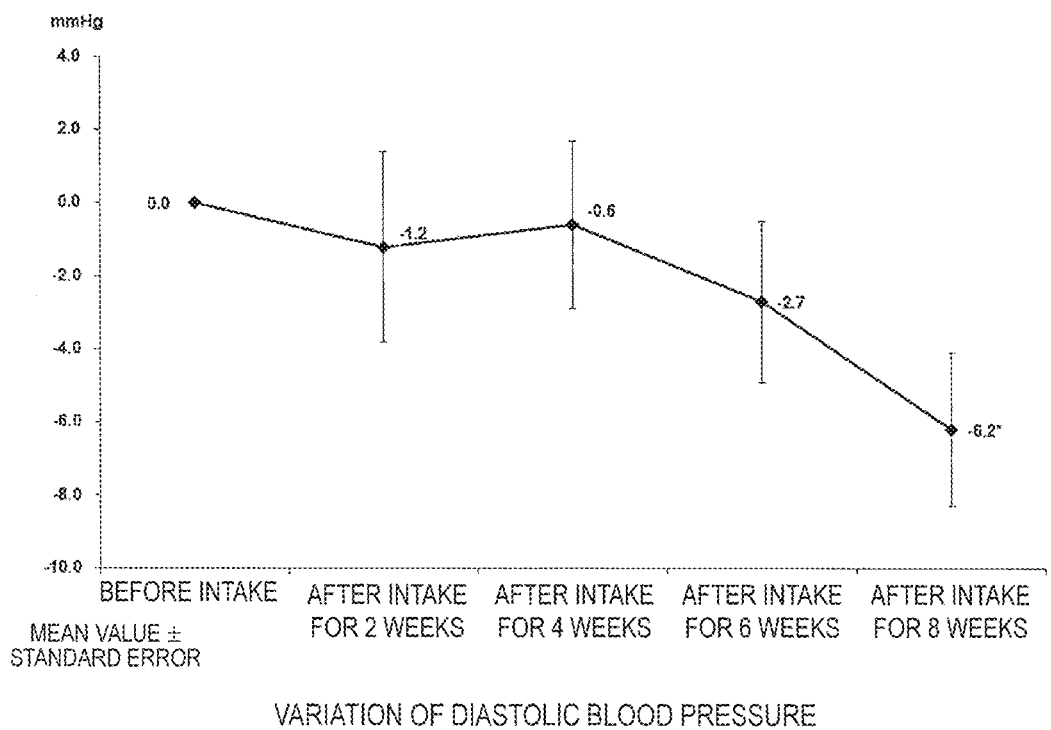
FIG. 8 This is a graph showing variations of a diastolic blood pressure, after intake of protease-degraded product-containing capsules for a predetermined period of time.

The blood pressure of each test subject was measured before the start of intake of the protease-degraded product-containing capsules and in 2 weeks, 4 weeks, 6 weeks and 8 weeks after the start of intake, using an electronic manometer (H55 Elemano blood-pressure gauge, manufactured by Terumo Corporation), and the diastolic blood pressure after the lapse of each intake period and the diastolic blood pressure before intake were compared according to a t-test. Based on the data before the start of intake, the variations of the diastolic blood pressure after the lapse of each intake period are shown in FIG. 8.

The diastolic blood pressure was 75.7±3.2 mmHg before intake, 74.5±3.7 mmHg after intake for 2 weeks, 75.1±3.6 mmHg after intake for 4 weeks, 73.0±3.2 mmHg after intake for 6 weeks, and 69.5±3.3 mmHg after intake for 8 weeks. As shown in FIG. 8, the variations based on the data before intake were −1.2±2.6 mmHg after intake for 2 weeks, −0.6±2.3 mmHg after intake for 4 weeks, −2.7±2.2 mmHg after intake for 6 weeks, and −6.2±2.1 mmHg after intake for 8 weeks. In time-dependent comparison, a significant decrease was recognized after intake for 8 weeks, as compared with the data before intake.

The above results confirm that the protease-degraded product that the composition of the present invention contains remarkably exhibits a knee joint pain relieving effect, a low back pain relieving effect, a knee joint motion range increasing effect, a cholesterol-lowering effect, a hypoglycemic effect and a diastolic blood pressure-lowering effect.

Though not clear, the mechanism of the freeze-dried powder of the protease-degraded product to exhibit these effects is presumed to be as follows.

First, regarding the pain relieving effect and the joint function ameliorating effect, it is presumed that the low-molecular hyaluronic acid that the protease-degraded product contains can ameliorate the lubricity of joints and can effectively contribute toward protecting and inhibiting destruction of joint cartilage, promoting cartilage differentiation, and protecting synovial cells, and further can function to suppress inflammations, therefore inducing these effects.

Regarding the diastolic blood pressure-lowering effect, it may be considered that the effect would be provided mainly by the influence of the pain relieving effect of the protease-degraded product. Specifically, the sympathetic nervous excitation that has been predominant owing to joint pain or low back pain could be suppressed by the pain relieving effect of the protease-degraded product, therefore resulting in reduction in diastolic blood pressure.

Regarding the total cholesterol level-lowering effect and the blood sugar level-lowering effect, it is presumed that the components that the protease-degraded product contains would have some beneficial influences on intestinal bacterial flora and serum cholesterol metabolism.

INDUSTRIAL APPLICABILITY

According to the present invention, there can be provided a composition having a pain relieving effect, a joint function ameliorating effect, a cholesterol-lowering effect, a hypoglycemic effect and a diastolic blood pressure-lowering effect at low cost. Consequently, using the composition of the present invention, there can be provided an inexpensive internal agent capable of relieving age-related decline in physical function. Accordingly, the industrial applicability of the present invention is great.

The invention claimed is:

1. A method for relieving a low back pain, lowering a cholesterol level in blood, lowering a sugar level in blood or lowering a diastolic blood pressure, which comprises orally administering to a patient in need thereof a pharmaceutically effective amount of a product obtained by degrading a comb with a protease so that content of a low-molecular hyaluronic acid having a molecular weight of 380 to 5000 is 10% by mass or more relative to the total amount of the product.

2. The method according to claim 1, which is for lowering a cholesterol level in blood in a patient in need thereof.

3. The method according to claim 1, which is for lowering a sugar level in blood in a patient in need thereof.

4. The method according to claim 1, which is for lowering a diastolic blood pressure in a patient in need thereof.

5. The method according to claim 1, wherein the proportion of a low-molecular hyaluronic acid having a molecular weight of 1520 to 5000 is 60% by mass or more of the total amount of the low-molecular hyaluronic acid having a molecular weight of 380 to 5000.

6. The method of claim 1, which is for relieving a low back pain in a patient suffering from low back pain.

* * * * *